United States Patent [19]

Vanlaningham

[11] Patent Number: 5,658,293
[45] Date of Patent: Aug. 19, 1997

[54] GUIDE PLATFORM ASSOCIATED WITH INTRAMEDULLARY ROD

[75] Inventor: Richard D. Vanlaningham, Milford, Ind.

[73] Assignee: Zimmer, Inc., Warsaw, Ind.

[21] Appl. No.: 544,419

[22] Filed: Oct. 10, 1995

[51] Int. Cl.⁶ .................................................. A61B 17/56
[52] U.S. Cl. ................................................ 606/88; 606/102
[58] Field of Search ................................ 606/88, 87, 89, 606/86, 96, 79, 80, 82, 102

[56] References Cited

U.S. PATENT DOCUMENTS

| | | |
|---|---|---|
| 4,457,307 | 7/1984 | Stillwell . |
| 4,459,985 | 7/1984 | McKay et al. . |
| 4,467,801 | 8/1984 | Whiteside . |
| 4,487,203 | 12/1984 | Androphy . |
| 4,567,885 | 2/1986 | Androphy . |
| 4,574,794 | 3/1986 | Cooke et al. . |
| 4,703,751 | 11/1987 | Pohl ............................ 606/87 |
| 4,721,104 | 1/1988 | Kaufman et al. . |
| 4,722,330 | 2/1988 | Russell et al. . |
| 4,759,350 | 7/1988 | Dunn et al. . |
| 4,787,383 | 11/1988 | Kenna . |
| 4,892,093 | 1/1990 | Zarnowski et al. ........... 606/82 |
| 4,926,847 | 5/1990 | Luckman ..................... 606/88 |
| 4,952,213 | 8/1990 | Bowman et al. ............. 606/79 |
| 5,035,699 | 7/1991 | Coates ........................ 606/86 |
| 5,047,032 | 9/1991 | Jellicoe ...................... 606/83 |
| 5,053,037 | 10/1991 | Lackey ........................ 606/79 |
| 5,092,869 | 3/1992 | Waldron ...................... 606/82 |
| 5,098,436 | 3/1992 | Ferrante et al. ............. 606/88 |
| 5,112,336 | 5/1992 | Krevolin et al. ............. 606/96 |
| 5,122,144 | 6/1992 | Bert et al. .................... 606/88 |
| 5,129,907 | 7/1992 | Heldreth et al. ............. 606/80 |
| 5,129,908 | 7/1992 | Petersen ...................... 606/80 |
| 5,171,244 | 12/1992 | Caspari et al. ............... 606/88 |
| 5,171,276 | 12/1992 | Caspari et al. ............... 623/16 |
| 5,176,684 | 1/1993 | Ferrante et al. ............. 606/86 |
| 5,180,384 | 1/1993 | Mikhail ........................ 606/80 |
| 5,190,547 | 3/1993 | Barber et al. ................ 606/79 |
| 5,201,768 | 4/1993 | Caspari et al. ............... 623/20 |
| 5,207,680 | 5/1993 | Dietz et al. ................. 606/86 |
| 5,207,711 | 5/1993 | Caspari et al. ............... 623/20 |
| 5,228,459 | 7/1993 | Caspari et al. .............. 128/898 |
| 5,234,433 | 8/1993 | Bert et al. .................... 606/88 |
| 5,263,498 | 11/1993 | Caspari et al. . |
| 5,304,181 | 4/1994 | Caspari et al. ............... 606/80 |
| 5,344,423 | 9/1994 | Dietz ........................... 606/87 |
| 5,411,505 | 5/1995 | Mumme ....................... 606/88 |
| 5,417,695 | 5/1995 | Axelson, Jr. ................. 606/89 |
| 5,454,816 | 10/1995 | Ashby ......................... 606/88 |
| 5,562,674 | 10/1996 | Stalcup et al. .............. 606/88 |

FOREIGN PATENT DOCUMENTS

| | | |
|---|---|---|
| 0 104 732 | 4/1984 | European Pat. Off. . |
| 340 176 | 11/1989 | European Pat. Off. . |
| 555003 | 8/1993 | European Pat. Off. ........ 606/88 |

*Primary Examiner*—Guy V. Tucker
*Attorney, Agent, or Firm*—Todd A. Dawson

[57] ABSTRACT

The invention is directed to an intramedullary rod guide assembly for use in orthopaedic surgery for aligning a cutting or milling guide platform. A guide platform is pivotally connected to an intramedullary rod intermediate the proximal and distal ends thereof. A threaded alignment mechanism aligns the guide platform relative to the intramedullary rod.

8 Claims, 2 Drawing Sheets

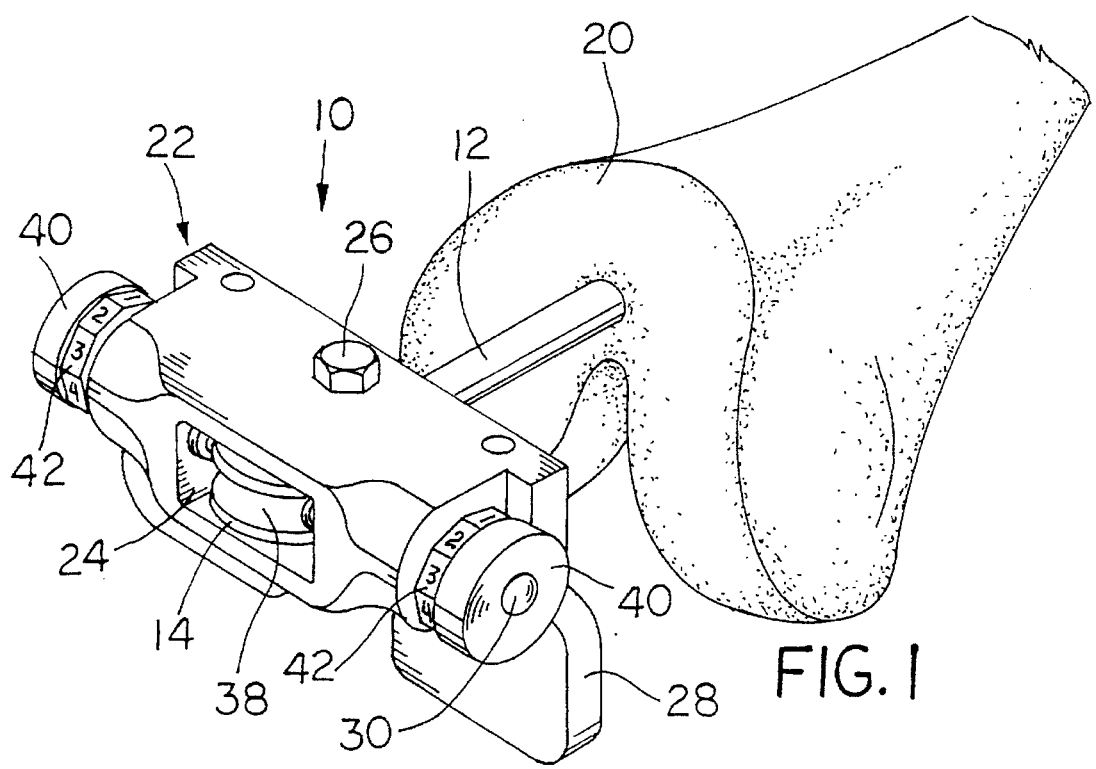
FIG. 1
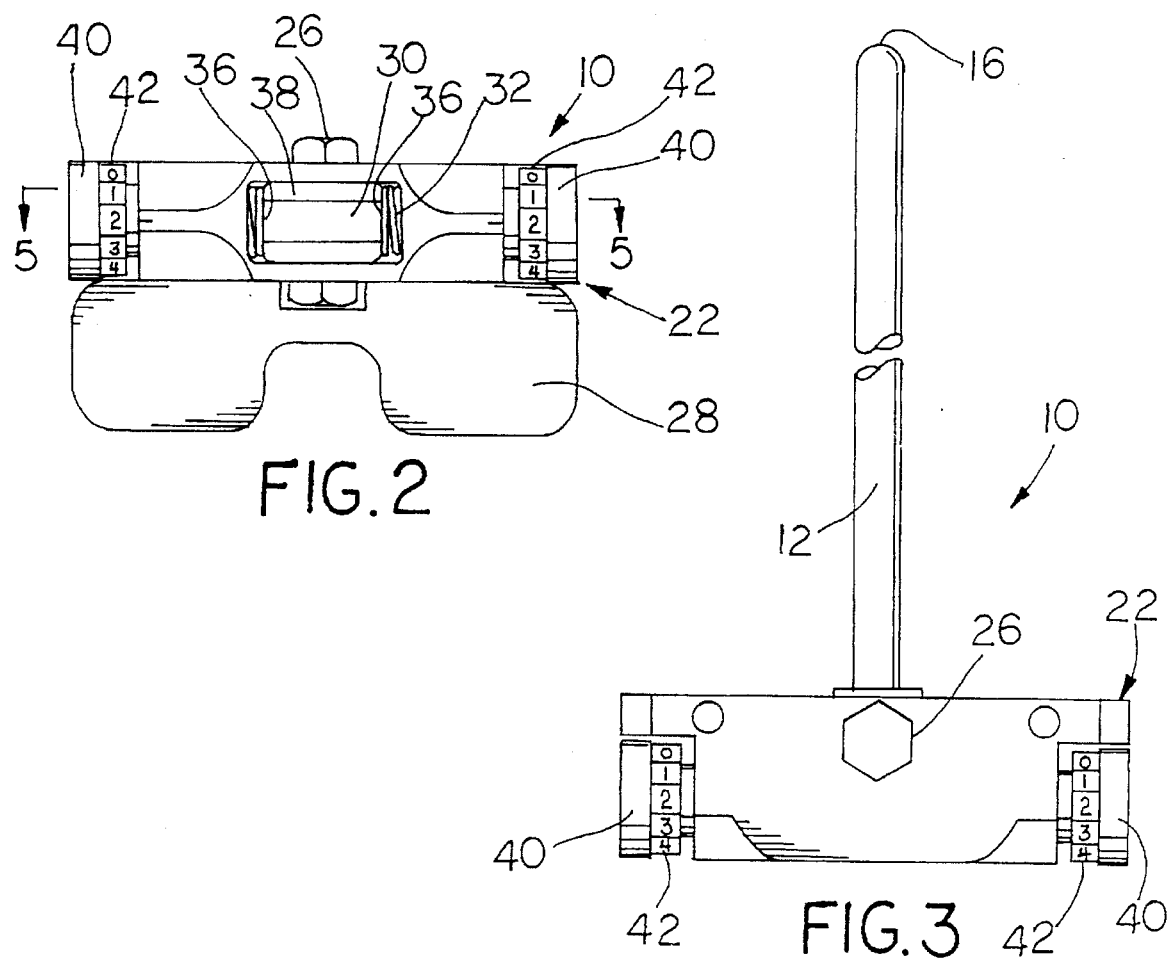
FIG. 2
FIG. 3

GUIDE PLATFORM ASSOCIATED WITH INTRAMEDULLARY ROD

BACKGROUND OF THE INVENTION

1. Field of the invention

The present invention relates to instrumentation used in orthopaedic surgery, and, more particularly, to instrumentation for aligning milling guide platforms and tools used to prepare bone for receiving a prosthesis.

2. Description of the related art

In an orthopaedic surgery to replace part or all of a patient's joint with a prosthetic implant, a portion of the implant receiving bone is prepared to closely match the mating surfaces of the implant. During an orthopaedic surgery to replace a knee joint, the distal end of the femur is prepared to accommodate a femoral knee component and the proximal end of the tibia is prepared to accommodate a tibial component.

Depending on the type of femoral implant to be accommodated by the femur, and the particular side of body with which the implant is to be mated, there are a small range of angles to which the implant must be oriented relative to the mechanical axis of the bone. Typically, in the preparation of the femur, for example, one or more cutting guides are placed adjacent the distal femur in a specific order to resect portions of the femur in succession. These cutting guides are generally individually aligned by the surgeon with reference to specific anatomic landmarks and a guide platform connected to an intramedullary rod.

What is needed in the art is an intramedullary rod with an attached guide mechanism to align the cutting or milling guide platform at a predetermined angle relative to the mechanical axis of the bone.

SUMMARY OF THE INVENTION

The present invention provides an intramedullary rod assembly with a guide mechanism that aligns the guide platform member and other instruments to the bone receiving a prosthesis. The platform member is pivotally attached to the intramedullary rod and a threaded mechanism rotates within the intramedullary rod or platform to pivot the platform relative the intramedullary rod and thereby set an angle therebetween.

An advantage of the intramedullary guide rod assembly of the present invention is that precise angular adjustment between the intramedullary rod and platform is possible due to rotation of a threaded shaft. Indicia marks on the thread shaft or platform indicate to the doctor the angle between the intramedullary rod and platform member.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a perspective view of one form of the present invention;

FIG. 2 is a top plane view of the invention of FIG. 1;

FIG. 3 is a fragmentary front view of the invention of FIG. 1;

DETAILED DESCRIPTION OF THE INVENTION

Figure 4:
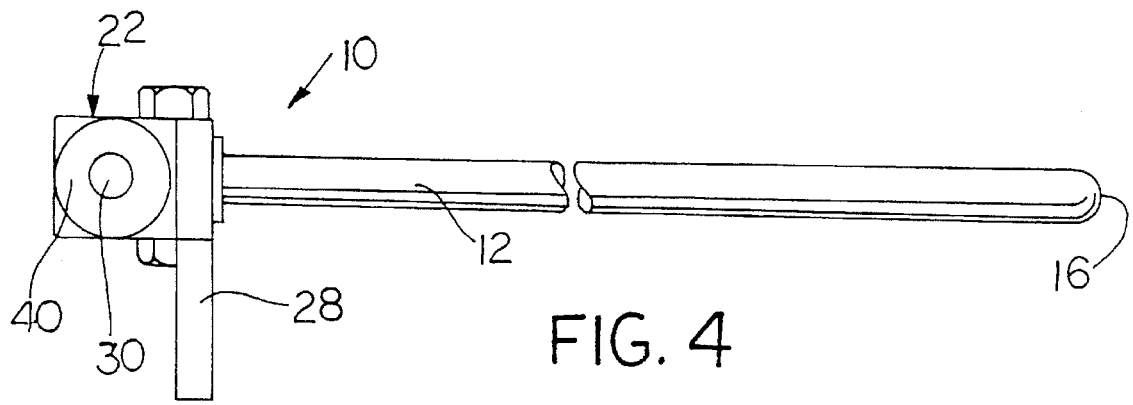
FIG. 4 is a fragmentary side elevational view of the invention in FIG. 1.
Figure 5:
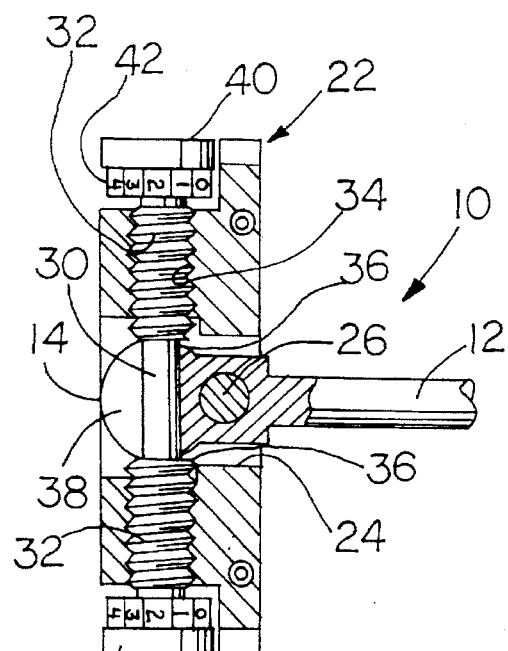
FIG. 5 is a fragmentary cross-sectional view taken along line 5—5 in FIG. 2 and viewed in the direction of the arrows.

Referring now to the drawings and particularly to FIGS. 1 and 5, an embodiment of an intramedullary guide rod assembly 10 of the present invention is shown. In general, intramedullary guide rod assembly 10 includes an intramedullary rod 12 having a proximal end 14 and a distal end 16. During an orthopedic operation, proximal end 14 is normally hit with a hammer to drive the intramedullary rod assembly 10 into a bone, such as a femur 20.

Guide platform or base 22, utilized for aligning milling and cutting guides to a bone, is pivotally attached by a pivot, such as a pin or bolt 26, to intramedullary rod 12 at a location which is preferably intermediate proximal end 14 and distal end 16. Platform 22 is utilized for establishing a reference point relative to the bone to be milled and may include extending arms (not shown), extending surfaces 28 or other structures to which additional cutting or milling guides (not shown) attach.

Platform 22 includes a central opening 24 for accommodating intramedullary rod 12 therethrough. Fixation pins (not shown), as known in the art, may also be used to temporarily affix platform 22 to bone 20.

For further details of the milling and cutting alignment guides attachable to guide platform 22, and use of an intramedullary rod, reference is made to co-pending U.S. patent application Ser. No. 08/169,459, which is assigned to the assignee of the present invention and hereby expressly incorporated herein by reference.

As depicted in FIG. 5, pivoting of guide platform 22 about pivot 26 is controlled by a threaded adjustment device. In the embodiment shown, the threaded adjustment device comprises a threaded shaft 30 having threads 32 thereon for fixating the relative angular position between platform 22 and intramedullary rod 12. Threaded shaft 30 is disposed in a threaded bore 34 formed in platform 22 substantially transverse to intramedullary rod 12.

Two spaced apart shoulders 36 are formed on threaded shaft 30 and engage intramedullary rod 12 on opposite sides thereof. These shoulders 36 are utilized to engage intramedullary rod 12 and force guide platform 22 to pivot when threaded shaft 30 is rotated. To ensure that shoulders 36 are always in contact with intramedullary rod 12 at all possible angular orientations, intramedullary rod 12 includes a circular cam member 38 either integrally formed therewith or attached thereto. As platform 22 pivots about pivot 26, shoulders 36 engage different areas of cam 38.

In the particular embodiment shown in FIGS. 1, 2, 5, and 6, threaded shaft 30 passes through cam 38, although it is not necessarily for operation. As long as shoulders 36 engage on opposite sides of cam 38, rotation of shaft 30 causes platform member 22 to pivot about pivot 26.

One or more knurled knobs 40 are attached to threaded shaft 30 to allow a surgeon to manually rotate shaft 30. Various indicia 42 such as numbers or degree markings may be inscribed on knobs 40 to permit the surgeon to determine the relative position of shaft 30, and therefore the relative angle between intramedullary rod 12 and guide platform member 22.

Figure 6:
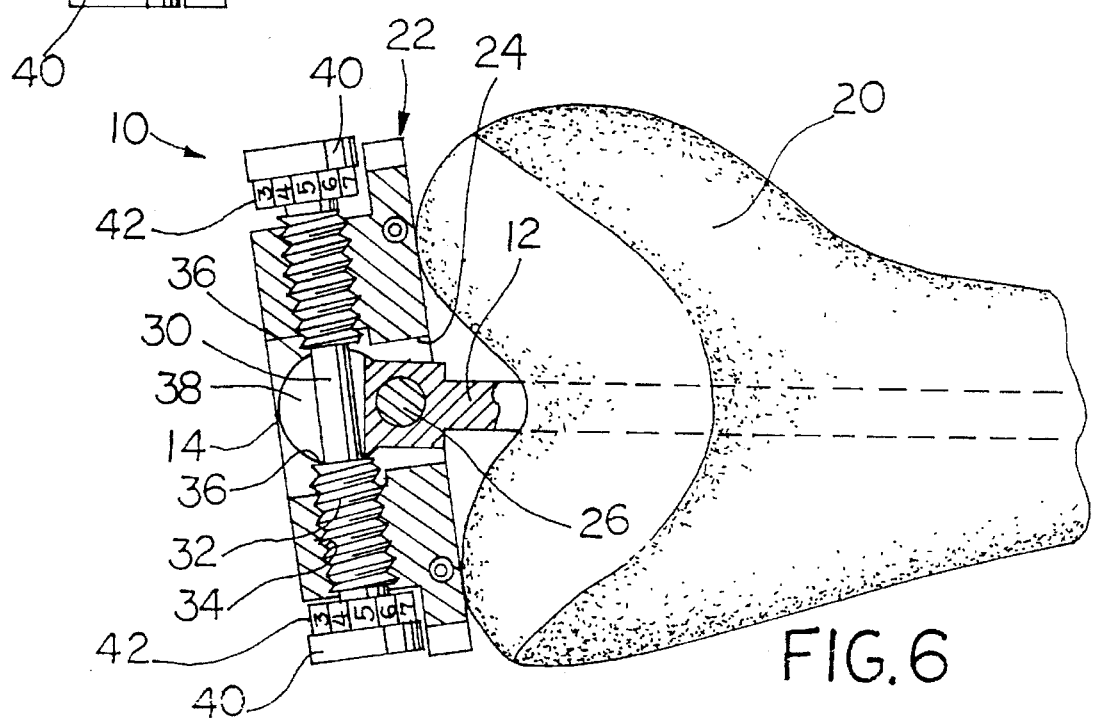
FIG. 6 is a fragmentary cross-sectional view similar to that of FIG. 5 illustrating the invention engaged within a bone.

In operation, a threaded device, such as threaded shaft 30 of the present invention, enables a surgeon to select a particular angular position between guide platform member 22 and intramedullary rod 12. More particularly, the surgeon first rotates knob 40, which thereby causes threaded shaft 30 to rotate and translate axially by engagement with the threads in threaded bore 34. Shoulders 36, carried or formed on shaft 30 and engaging cam 38, likewise translate axially and force is exerted on cam 38 in one axial direction or another. This pressure or force causes guide platform 22 to pivot in an opposite direction about pivot 26, thereby changing the relative angle between intramedullary rod 12 and guide platform 22. After the surgeon has changed the relative angle between intramedullary rod 12 and guide platform 22 to meet specific requirements, intramedullary rod assembly 10 is fully inserted into bone 20 (FIG. 6).

Alternatively and equivalently, the system as shown may be mechanically reversed such that shaft 30 is threadedly engaged through intramedullary rod 12 and shoulder portions on shaft 30 (not shown) engage portions of guide platform 22. Rotation of shaft 30 would cause relative angular movement between intramedullary rod 12 and guide platform 22.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An intramedullary rod assembly, comprising:
   an intramedullary rod having a distal end and proximal end;
   a platform member pivotally attached to said intramedullary rod between said distal end and said proximal end; and
   threaded means, connected to at least one of said intramedullary rod and said platform member, and being rotatable relative to said platform member, for forcing said platform member to pivot relative to said intramedullary rod, whereby the relative angle between said platform member and said intramedullary rod may be adjusted,
   wherein said intramedullary rod includes a cam that abuts said threaded means, and
   wherein said threaded means comprises a shaft having two spaced apart shoulders, said cam disposed between said shoulders.

2. The intramedullary rod assembly of claim 1, wherein said shaft moves along its longitudinal axis when rotated, whereby at least one of said shoulders forces said platform member to pivot relative to said intramedullary rod.

3. The intramedullary assembly of claim 1, wherein said threaded means includes indicia for measuring the rotational position of said threaded means.

4. The intramedullary rod assembly of claim 1, wherein rotation of said threaded means forces said platform member to pivot as a result of positive engagement between said platform member and said intramedullary rod.

5. An intramedullary rod assembly, comprising
   an intramedullary rod having a distal end and proximal end;
   a platform member pivotally attached to said intramedullary rod; and
   a threaded shaft, connected to at least one of said intramedullary rod and said platform member, and being rotatable relative to said platform, said shaft having a shoulder that engages said intramedullary rod, whereby upon rotation of said shaft, said shoulder forces said platform member to pivot relative to said intramedullary rod, such that the relative angle between said platform member and said intramedullary rod is adjusted,
wherein said shaft includes two spaced apart shoulders, said intramedullary rod being disposed between said shoulders.

6. The intramedullary rod assembly of claim 5, wherein said intramedullary rod includes a cam that engages said shoulder.

7. The intramedullary rod assembly of claim 5, wherein said shaft moves along its longitudinal axis when rotated, whereby at least one of said shoulders force said platform member to pivot relative to said intramedullary rod.

8. The intramedullary assembly of claim 1, wherein said threaded means includes indicia for measuring the rotational position of said threaded means.

* * * * *